United States Patent
Roberts

Patent Number: 5,406,941
Date of Patent: Apr. 18, 1995

[54] ADJUSTABLE CURVATURE LARYNGOSCOPE BLADE

[76] Inventor: James T. Roberts, 901 Charles River St., Nedham, Mass. 02192

[21] Appl. No.: 9,689

[22] Filed: Jan. 27, 1993

[51] Int. Cl.⁶ .......................... A61B 1/267; A61B 1/07
[52] U.S. Cl. ........................................ 128/11; 15/235.8; 128/10; D24/135
[58] Field of Search ................... 128/10, 11, 3, 15, 16, 128/17, 18, 23, 20; 606/198; 604/105, 109; 15/235.4–235.8; D24/135–137

[56] References Cited

U.S. PATENT DOCUMENTS

| | | | |
|---|---|---|---|
| 1,212,826 | 1/1917 | Smith | 15/235.8 |
| 2,912,851 | 11/1958 | Karnes | 15/235.5 |
| 3,123,947 | 3/1964 | Rawley | 15/235.8 |
| 3,315,664 | 4/1967 | Hill | 128/15 |
| 3,913,568 | 10/1975 | Carpenter | 128/11 |
| 3,986,854 | 10/1976 | Scrivo et al. | 128/11 X |
| 4,314,551 | 2/1982 | Kadell | 128/11 |
| 4,337,761 | 7/1982 | Upsher | 128/11 |
| 4,360,008 | 11/1982 | Corazzelli, Jr. | 128/11 |
| 4,565,187 | 1/1986 | Soloway | 128/11 |
| 4,573,451 | 3/1986 | Bauman | 128/11 |
| 4,669,970 | 6/1987 | Perry | 15/235.7 |
| 5,003,962 | 4/1991 | Choi | 128/10 X |
| 5,192,558 | 3/1993 | Sparrow et al. | 15/235.8 X |

FOREIGN PATENT DOCUMENTS

630051  8/1927  France ........................ 15/235.8

Primary Examiner—Richard J. Apley
Assistant Examiner—Donna L. Maraglio
Attorney, Agent, or Firm—Fishman, Dionne & Cantor

[57] ABSTRACT

A laryngoscope for use in endotracheal intubation wherein the blade is adjustable between a straight surface and a curved surface.

6 Claims, 2 Drawing Sheets

ADJUSTABLE CURVATURE LARYNGOSCOPE BLADE

BACKGROUND OF THE INVENTION

The present invention relates to laryngoscopes which are primarily used for performing endotracheal intubation. Specifically, the present invention relates to a laryngoscope which has a blade that can be adjusted between a straight surface and a curved surface.

Laryngoscopes are generally considered to be examining or viewing devices which comprise a blade, either straight or curved, affixed to a handle in a generally L-shaped configuration. When using such a device, for example, to view the larynx, the upper surface of the blade adjacent the handle is used to depress the tongue and mandible of a patient in a supine position in order to prevent the patient's tongue from obstructing the view during the examination. Depending upon the preference of the physician/anesthesiologist, the laryngoscope used may have a straight blade or a curved blade. In some instances, the physician/anesthesiologist may use both types as well as laryngoscopes having blades of varying length so as to be able to accommodate different pharangeal configurations of various patients.

While there have been attempts to provide laryngoscopes with a degree of adjustability such as shown in U.S. Pat. Nos. 4,314,551, 4,337,761, 4,360,008 and 4,573,451, said attempts are primarily concerned with hinged attachment of the laryngoscope blade to a handle or the like and/or pivotal movement of a portion of the laryngoscope blade.

SUMMARY OF THE INVENTION

The present invention is directed to a laryngoscope which has a blade that may be infinitely adjusted between a flat configuration and final curved configuration.

In accordance with the present invention, a laryngoscope blade produced from a flexible material is provided with means which when moved clockwise or counterclockwise relative to the longitudinal axis of said blade, cams said blade into a curved configuration and vice versa.

In addition to the above, the means for changing the configuration of the laryngoscope blade is also capable of receiving and positioning a plurality of fiber optic bundles for use in visualization and light transmission purposes.

The present invention will be more fully understood by reference to the following detailed description when considered in conjunction with the accompanying drawings.

DESCRIPTION OF THE PREFERRED EMBODIMENT

Figure 1:
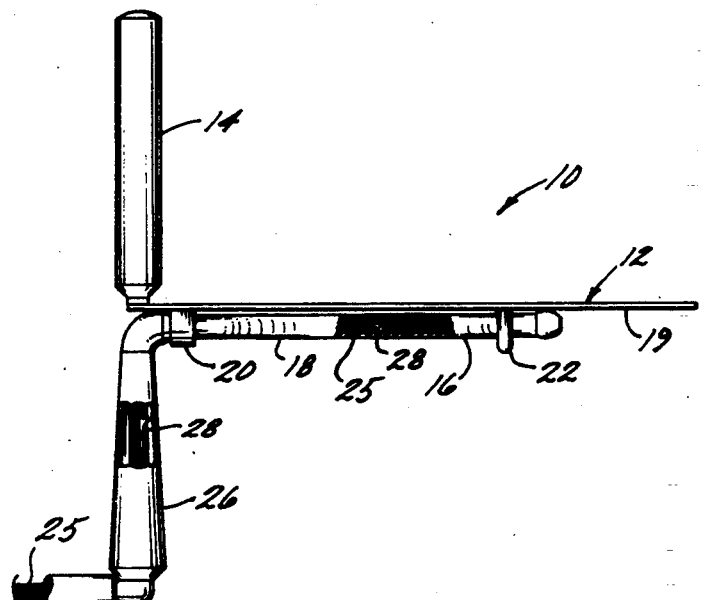
FIG. 1 is a side elevation view of the laryngoscope of the present invention with the blade in a flat, straight configuration.

With reference to all of the drawings in this case, the laryngoscope of the present invention is shown at 10. As shown in FIG. 1, the laryngoscope 10 comprises a flexible blade 12 which is affixed to a handle 14 adjacent the proximate end of the blade 12. The blade 12 may be produced from a suitable flexible material, such as spring steel or plastic, which is capable of being bent into an arcuate configuration from a flat, substantially straight configuration and returned to a flat, substantially straight configuration. As further shown, the proximate end of the blade 12 is attached to a handle 14 which is positioned substantially perpendicular to the blade 12 when it lies flat.

Figure 3:
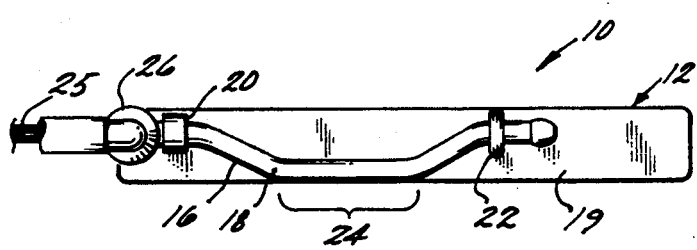
FIG. 3 is a bottom view of the laryngoscope of the present invention as shown in FIG. 1.
Figure 4:
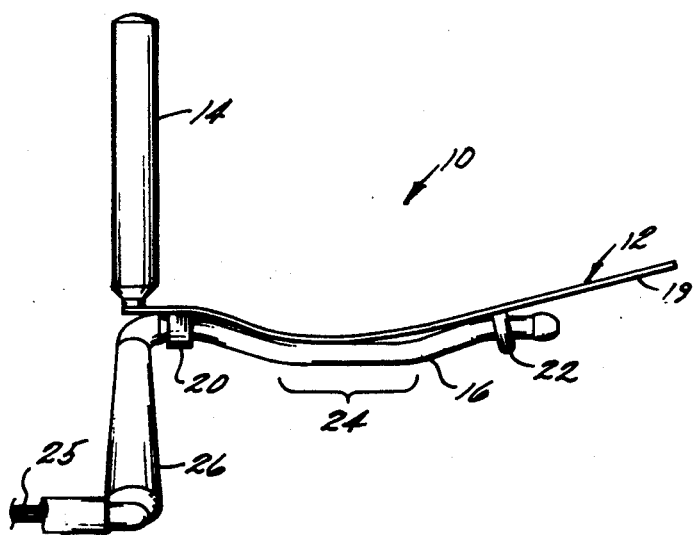
FIG. 4 is a side elevation view of the laryngoscope of the present invention with the blade in a curved configuration.
Figure 5:
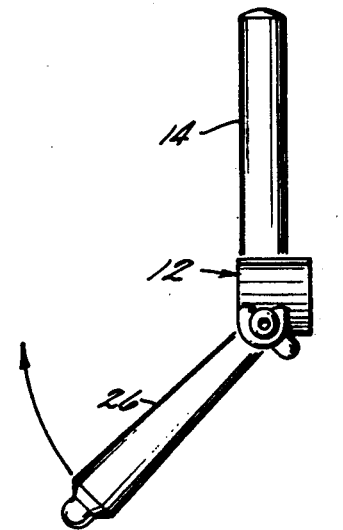
FIG. 5 is an elevation view of the laryngoscope of the present invention as shown in FIG. 4 and taken from the distal end of the blade.

As best seen in FIGS. 1 and 3, means for changing the configuration of the blade 12 is shown at 16. Such means includes a camming member 18 affixed to one of the surfaces 19 of the blade 12 via straps 20 and 22. The camming member 18 is generally in a U-shape with the bight or bend portion 24 disposed between the straps 20 and 22. A camming handle 26 is provided on the proximate end of the camming member 18 and is used to turn said member relative to the flat surface 19 of the blade to which it is attached. As the camming member 18 is rotatable within said straps, 20 and 22, rotation of the camming member 18 will cause a change in the configuration of the blade 12 as will be described below.

While the camming member 18 and the camming handle 26 may be made of any suitable material, it has been found that when said member 18 and camming handle 26 are provided with a passageway or conduit through their lengths, such as shown at 28, said passageway or conduit may be employed to receive a fiber optic bundle 25 for visualization and light transmission purposes. The use of fiber optic bundles for said purposes is well-known in the art.

Figure 2:
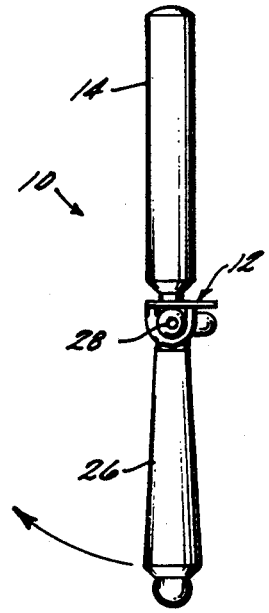
FIG. 2 is an elevation view of the laryngoscope of the present invention taken from the distal end of the blade.
Figure 6:
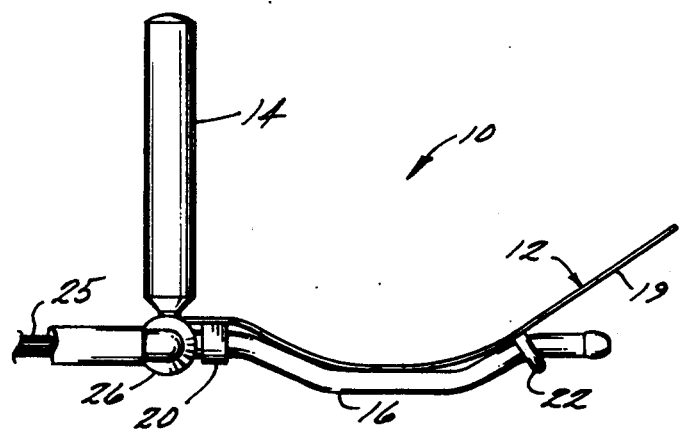
FIG. 6 is a side elevation view of the laryngoscope of the present invention with the blade in its maximum curved configuration.

In using the laryngoscope of the present invention, the physician may begin the insertion of the blade into a patient's mouth with the blade 12 in a flat configuration or a curved configuration depending upon the physician's preference. In the instance where the blade 12 is in a flat configuration as shown in FIGS. 1, 2 and 3, the blade configuration may be changed to a curved configuration by rotating the camming handle 26 in a clockwise direction as shown by the arrow in FIG. 2. Such rotation causes the camming member 18 to rotate within straps 20 and 22 thereby forcing the blade to bend into the bight position of the camming member 18 thus forming the blade 12 in a curved configuration. Further clockwise rotation of the camming handle 26, i.e. to a full 90° position, provides a more curved configuration to the blade as shown in FIGS. 6 and 7.

Figure 7:
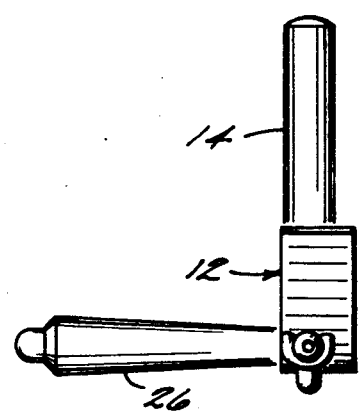
FIG. 7 is an elevation view of the laryngoscope of the present invention as shown in FIG. 6 taken from the distal end of the blade.

As should be clear to those skilled in the art, counterclockwise rotation of the camming handle 26 from the position shown in FIG. 7 will bring the blade back to a flat, straight configuration.

Although only a single embodiment of the present invention has been disclosed and described herein, it will be clear to those skilled in the art that changes may be made in the device of the present invention without departing from the spirit and scope of the invention.

I claim:

1. A laryngoscope comprising a flexible substantially flat, straight blade having a proximate edge and a distal edge, a handle disposed at the proximate edge of said blade on a first surface of said blade, means for changing the configuration of said blade between a substantially straight condition to a curved condition, said means being disposed on a second surface of said blade opposite said first surface of said blade, and means for activating said means for changing the configuration of said blade, said means for activating being disposed adjacent said means for changing the configuration of said blade.

2. The laryngoscope of claim 1 wherein said means for changing the configuration of said blade comprises a camming member rotatably disposed on said blade.

3. The laryngoscope of claim 2 where said camming member comprises an elongated tube having a passageway therethrough and a U-shaped bight therein, said elongated tube being rotatably disposed on said blade by straps disposed on each side of said U-shaped bight.

4. The laryngoscope of claim 3 wherein said means for activating said means for changing the configuration of said blade comprises a camming handle affixed to the proximate end of said elongated tube whereby rotation of said camming handle rotates said elongated tube in said straps.

5. The laryngoscope of claim 4 wherein said camming handle is provided with a passageway therethrough which is coaxial with the passageway in said elongated tube.

6. The laryngoscope of claim 5 wherein fiber optic bundles are disposed in the coaxial passageway through said camming handle and said elongated tube for visualization and light transmission purposes at the distal end of said blade.

* * * * *